US00PP28313P2

(12) United States Plant Patent
Ranney

(10) Patent No.: US PP28,313 P2
(45) Date of Patent: Aug. 22, 2017

(54) ***SPIRAEA* 'NCSX1'**

(50) Latin Name: *Spiraea*
Varietal Denomination: NCSX1

(71) Applicant: North Carolina State University, Raleigh, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 14/999,179

(22) Filed: Apr. 8, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

PLUTO Plant Variety Database Mar. 2, 2017. p. 1.*

* cited by examiner

*Primary Examiner* — Annette Para
(74) *Attorney, Agent, or Firm* — Cassandra Bright

(57) ABSTRACT

'NCSX1' is a new cultivar of hybrid *spiraea* that is a triploid selection with a compact habit and multicolored, yellow-orange foliage throughout the growing season with red-purple flowers.

3 Drawing Sheets

Latin name of the genus and species: The Latin name of the novel plant variety disclosed herein is *Spiraea.*

Variety denomination: The inventive hybrid of *Spiraea japonica* H2007-101-003 (unpatented, tetraploid)×*Spiraea* 'Zelda' (U.S. Plant Pat. No. 21,976 P2, diploid) disclosed herein has been given the varietal denomination 'NCSX1'.

BACKGROUND OF THE INVENTION

The present invention comprises a new and distinct hybrid *spiraea* cultivar hereinafter referred to by the cultivar name 'NCSX1'. This new *spiraea* was developed through a breeding program at North Carolina State University, Mills River, N.C. 'NCSX1' was selected from a population of seedlings grown from a controlled cross of *Spiraea japonica* H2007-101-003 (unpatented, tetraploid)×*Spiraea* 'Zelda' (U.S. Plant Pat. No. 21,976 P2, diploid). The first asexual propagation of 'NCSX1' was carried out in July 2012 by rooting stem cuttings at the North Carolina State University, Mountain Horticultural Crops Research Station, Mills River, N.C. and has been asexually reproduced repeatedly by vegetative cuttings over a 3 year period. 'NCSX1' roots readily from softwood cuttings treated with a basal dip of 4,000-5,000 ppm indole butyric acid (potassium salt) in water. 'NCSX1' has been found to retain its distinctive characteristics through successive asexual propagations.

SUMMARY OF THE INVENTION

The following are the unique combination of characteristics of this new cultivar when grown under standard horticultural practices at North Carolina State University, Mountain Horticultural Crops Research Station, Mills River, N.C.

1. Triploid with a 2C genome size of ~0.81 pg.
2. Attractive multicolored, yellow-orange foliage throughout the growing season.
3. Red-purple flower color.
4. Compact habit.

BRIEF DESCRIPTION OF THE DRAWINGS

This new *spiraea* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new hybrid *spiraea.*

DETAILED BOTANICAL DESCRIPTION

Figure 1:
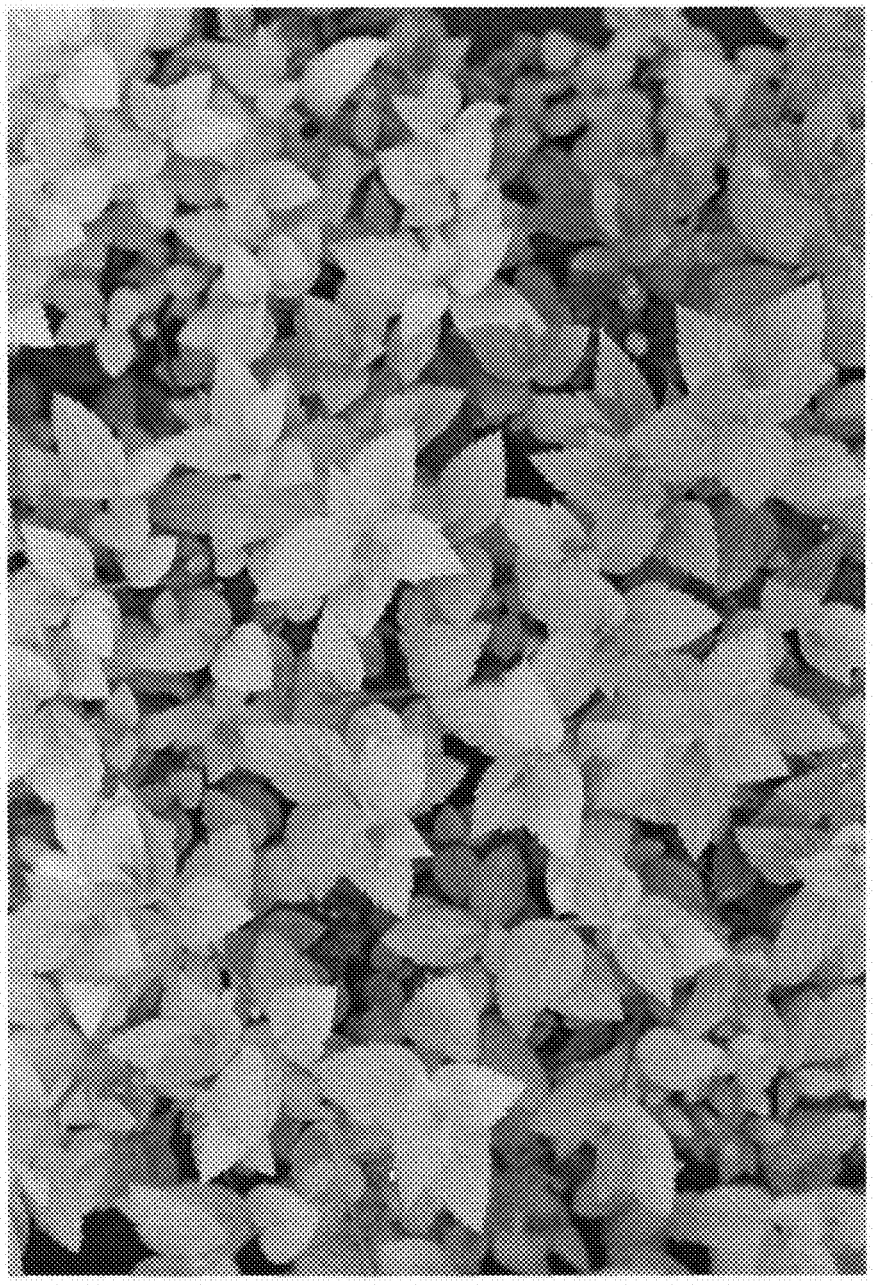
FIG. 1 is a color photograph showing the multicolored fall foliage of 'NCSX1' in Grand Haven, Mich. in the fall of 2015.
Figure 2:
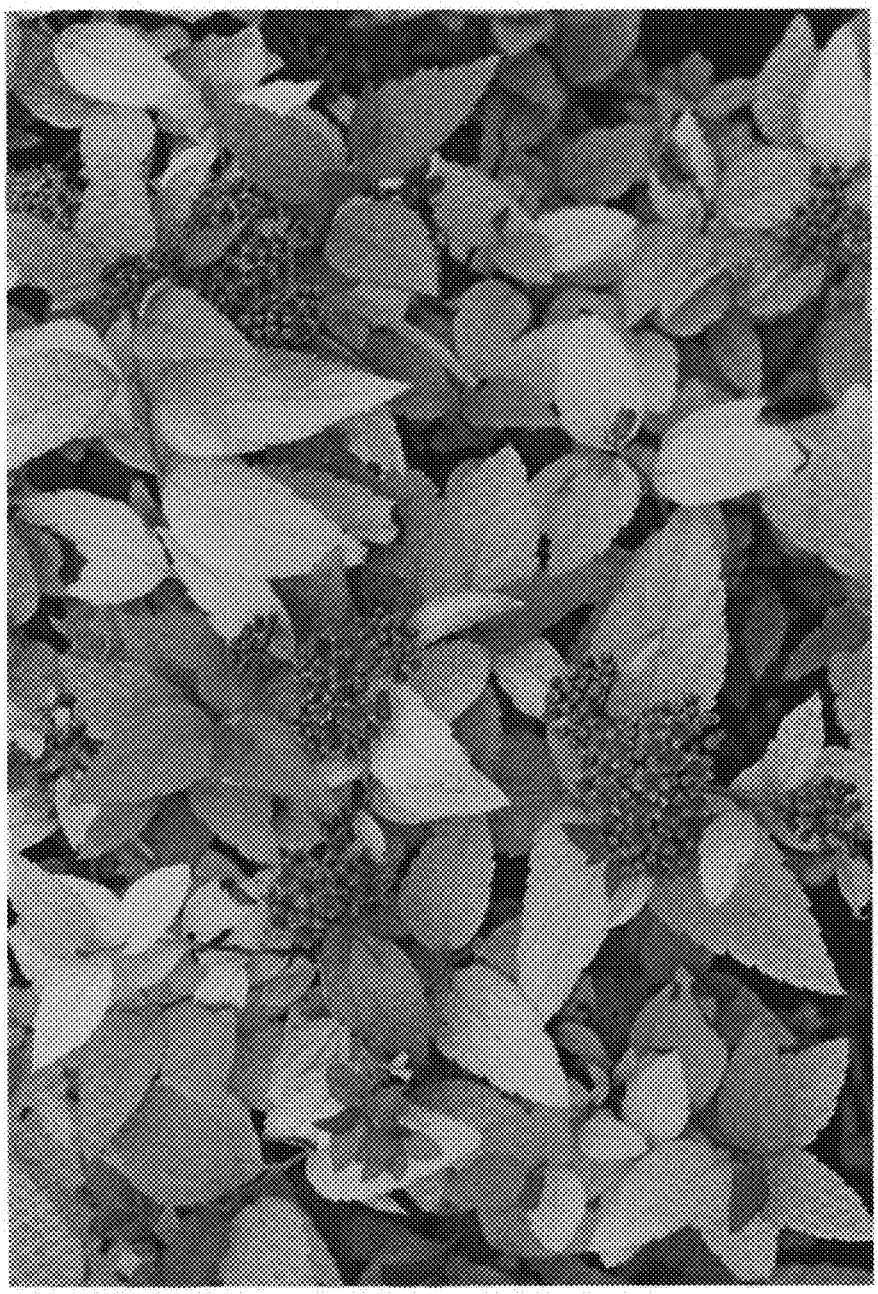
FIG. 2 is a color photograph showing the summer foliage and inflorescences of 'NCSX1' in Grand Haven, Mich. in the summer of 2015.
Figure 3:
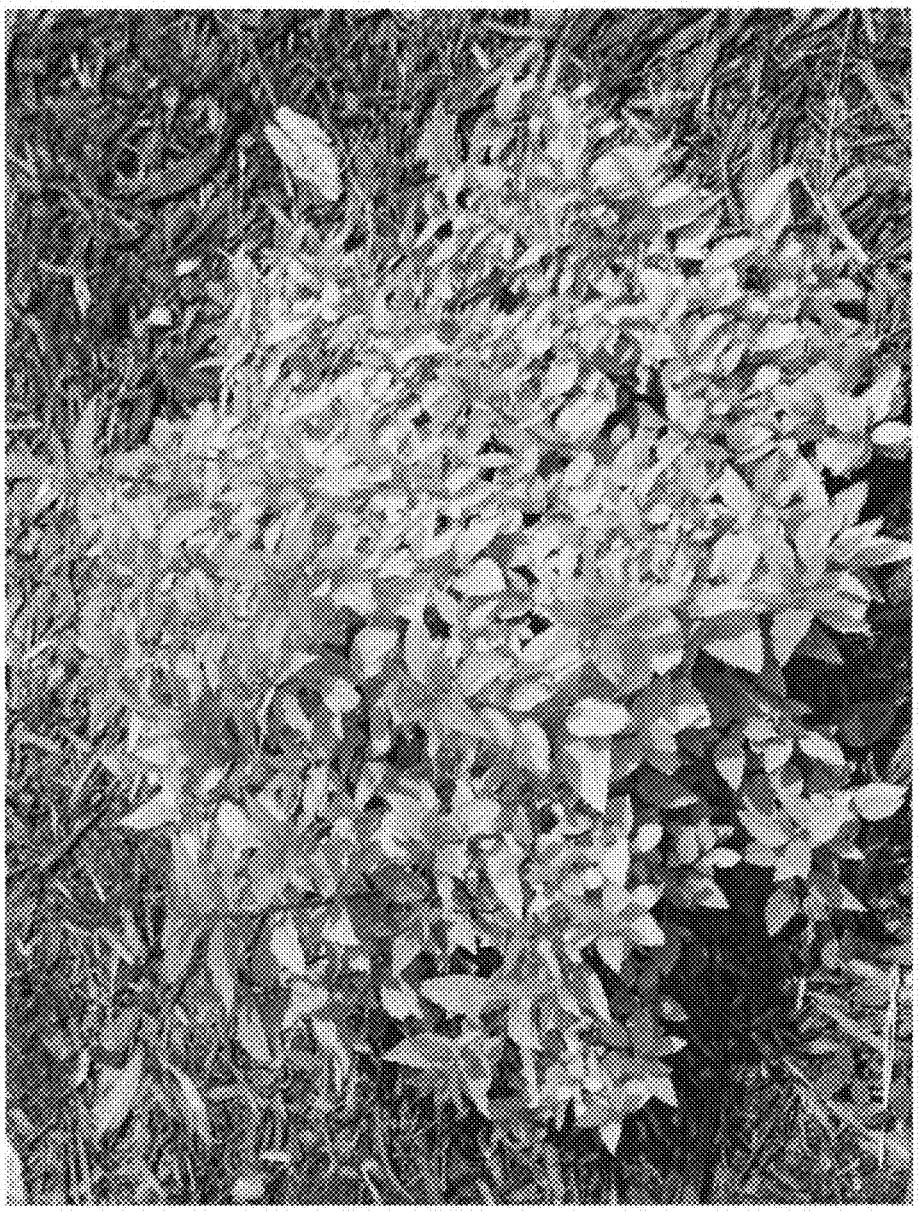
FIG. 3 is a color photograph of the habit and spring foliage colors of 'NCSX1' in Grand Haven, Mich. in the spring of 2015.

The following is a detailed description of the botanical characteristics of the new and distinct hybrid *spiraea* variety plant known by the denomination 'NCSX1'. The detailed description was taken on a three-year-old container-grown plant in Grand Haven, Mich. in 2015. All colors cited herein refer to The Royal Horticultural Society Colour Chart (The Royal Horticultural Society (R.H.S.), London, 2015 Edition). Where specific dimensions, sizes, colors, and other characteristics are given, it is to be understood that such characteristics are approximations or averages set forth as accurately as practicable.

Technical Description of the Variety

Classification:

*Botanical name.*—*Spiraea* 'NCSX1'.

*Common name.*—*Spiraea* or Spirea.

Parentage: Seedling grown from a controlled cross of *Spiraea japonica* H2007-101-003 (unpatented)×*Spiraea* (*fritschiana*×*japonica*) 'Zelda' (U.S. Plant Pat. No. 21,976 P2).

Plant description:

*Growth habit.*—Mounded.

*Height.*—46.0 to 61.0 cm.

*Width.*—46.0 to 61.0 cm.

Branches:

*Lateral branch diameter.*—About 0.3 cm.

*Lateral branch length.*—About 15 to 18 cm.

*Internode length.*—About 0.6 cm.

*Branch color.*—Immature: Close to Greyed-Yellow (160A). Mature: Greyed-Orange (165A).

*Branch texture.*—Pubescent.

Leaves:

*Type.*—Simple.

*Persistence.*—Deciduous.

*Arrangement.*—Alternate.

*Shape.*—Ovate.

*Apex.*—Acute.

*Base.*—Acute.

*Venation.*—Pinnate.

*Vein color.*—Upper: Spring top growth (top 1 to 2 leaves) Greyed-Red (178C); third to fourth leaf from the top is between Yellow-Green (153B) & Greyed-Orange (172C); fifth leaf (from the top) Yellow-Green (144B); sixth leaf (from the top) is close to Yellow-Green (145A); seventh to eighth leaf (from the top) is close to Yellow-Green (144B); most mature leaves (closest to the bottom of the branch) are closest to Yellow-Green (144A). Lower: Spring top growth (top 1 to 2 leaves) Greyed-Red (178C); third to fourth leaf from the top is between Yellow-Green (153B) & Greyed-Orange (172C); fifth to sixth leaf (from the top) are Yellow-Green (145A); seventh to eighth leaf (from the top) is close to Yellow-Green (145B); most mature leaves (closest to the bottom of the branch) are closest to Yellow-Green (144A).

*Margins.*—Serrate.

*Emerging leaves.*—Color: Upper: Spring top growth (top 1 to 2 leaves) Greyed-Red (178C); third to fourth leaf (from the top) is between Yellow-Green (153B) & Greyed-Orange (172C). Lower: Spring top growth (top 1 to 2 leaves) Greyed-Orange (175D) and Red Group (46A); third to fourth leaf (from the top) is between Yellow-Green (153B) & Greyed-Orange (166C). Texture: Rugose with puberulent lower side.

*Mature leaves during growing season.*—Color: Upper and lower: Fifth leaf from the top (on majority of the branches) is closest to Yellow-Green (145A); sixth leaf (from the top) is close to Yellow-Green (151B); seventh to eighth leaf (from the top) is close to Yellow-Green (144B); most mature leaves (closest to the bottom of the branch) are closest to Yellow-Green (144A). Texture: Rugose. Length of lamina: Avg. 65.5 mm (47.4 to 79.3 mm). Width: Avg. 26.9 mm (17.1 to 35.2 mm).

*Fall foliage color.*—After first frost foliage turns to a mixture of Red (45A), Yellow (B13), Greyed-Orange (169A), Greyed-Purple (184A) and Greyed-Purple (N186C).

*Leaf attachment.*—Petiolate.

*Petiole.*—Length: 0.3 cm. Diameter: 0.1 cm. Color: Spring top growth (top 3 to 4 leaves) are Greyed-Red (180C); fifth to sixth leaf (from the top) are Yellow-Green (151B); seventh to most mature leaves are close to Yellow-Green (151A). Texture: Glabrous.

Inflorescence:

*Description.*—Single whorled, rotate flowers arranged on a terminal corymb.

*Number of true flowers per inflorescence.*—About 50.

*Flowering season.*—Late spring through summer in Grand Haven, Mich.

*Fragrance.*—Slight, sweet fragrance.

*Inflorescence diameter.*—2.3 cm.

*Inflorescence height.*—1.5 cm.

*Bud.*—Shape: Globular. Length: 0.2 cm. Diameter: 0.2 cm. Color: Yellow-green (147C) at base and close to Red-Purple (59C) at tip.

*Perianth.*—Diameter: 0.6 cm. Height: 0.3 cm.

*Perianth aspect.*—Clustered, mostly outward facing.

*Petal.*—Arrangement: Whorl. Number: 5. Fused: Not fused. Texture: Glabrous. Shape: Globular. Margin: Entire. Apex: Obtuse. Base: Obtuse. Length: 0.2 cm. Width: 0.2 cm. Color when opening: Upper: Red-Purple (71B). Lower: Red-Purple (72D). Color at anthesis: Upper: Red-Purple (71B). Lower: Red-Purple (72D). Color fading to: Greyed-Orange (166D).

*Calyx.*—Shape: Cup-shaped with five lobes. Length: 0.2 cm. Diameter: 0.2 cm.

*Sepal.*—Arrangement: Single whorl. Number: 5. Texture: Glabrous. Shape: Acute. Margin: Entire. Apex: Acute Base: Fused. Color: Upper: Red-Purple (70C) with Red-Purple (58A) at apex. Lower: Red-Purple (70C) with Red-Purple (58A) at apex. Length: 0.15 cm. Width: 0.15 cm.

*Peduncle.*—Length: 0.5 cm. Diameter: 0.05 cm. Color: Yellow-Green (145C) blended with Red-Purple (61B). Surface texture: Glabrous.

*Pedicels.*—Length: 0.25 cm. Diameter: 0.05 cm. Texture: Glabrous. Color: Yellow-Green (145C) blended with Red-Purple (62B).

Reproductive organs:

*Gynoecium.*—Pistil number: 5. Pistil length: 0.2 cm. Stigma shape: Globose. Stigma color: Red-purple (60B). Style length: 0.5 mm. Style color: Red-Purple (60B). Ovary color: Red-Purple (60B).

*Androecium.*—Stamen number: 32. Anther shape: Globose. Anther size: 0.25 mm. Anther color: Black (202A). Filament length: 0.3 to 0.7 cm. Filament color: Red-Purple (61B). Amount of pollen: Very little. Pollen color: White (155D).

Fruit and seed: None observed.

DNA content: 2C DNA contend was determined following the methods of Shearer and Ranney (2013) using 4', 6-diamidino-2-phenylindole (DAPI) fluorochrome stain and *Pisum sativum* 'Ctirad' as an internal standard. Mean 2C DNA content for 'NCSX1' was 0.81 pg, which is consistent for a triploid based on research where 2C DNA contents for diploid *S. japonica* ranged from 0.52-0.61 pg (Wilson and Hoch, 2009).

Disease and insect resistance: No significant disease or insect pests have been observed.

Cold hardiness: At least USDA zone 5; testing has not been completed in colder zones.

COMPARISON WITH COMMERCIAL CULTIVARS

'NCSX1' is distinguished from commercial cultivars in that 'NCSX1' is a triploid selection whereas most other taxa of *S. japonica* including 'Albiflora', 'Anthony Waterer', 'Candlelight', 'Crispa', 'Dakota Goldcharm', var. alpina, 'Daphne', 'Darts Red', 'Flaming Mound', 'Flowering Choice', 'Froebelii', 'Golden Princess', 'Goldflame', 'Goldmound', 'Gumball', 'Lemon Princess', 'Little Princess', 'Magic Carpet', 'Neon Flash', 'Norma', and 'Shibori' are diploids while *S.j.* var. *fortunei* is a tetraploid (Wilson and Hoch, 2009).

CITATIONS

Shearer, K. and T. G. Ranney. 2013. Ploidy levels and relative genome sizes of species, hybrids, and cultivars of dogwood (*Corunus* spp.). HortScience 48(7):825-830.

Wilson, R. L. and W. A. Hoch. 2009. Identification of sterile, noninvasive cultivars of Japanese spirea. Hortscience 44(7):2031-2034.

What is claimed is:

1. A new and distinct hybrid *spiraea* plant named 'NCSX1' substantially as illustrated and described herein.

* * * * *